(12) United States Patent
Higgins

(10) Patent No.: US 9,750,525 B2
(45) Date of Patent: Sep. 5, 2017

(54) DEVICES, SYSTEMS AND METHODS FOR AN OSCILLATING CROWN DRIVE FOR ROTATIONAL ATHERECTOMY

(71) Applicant: Cardiovascular Systems, Inc., St. Paul, MN (US)

(72) Inventor: Joseph Peter Higgins, Minnetonka, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 205 days.

(21) Appl. No.: 14/208,585

(22) Filed: Mar. 13, 2014

(65) Prior Publication Data

US 2014/0316450 A1    Oct. 23, 2014

Related U.S. Application Data

(60) Provisional application No. 61/782,184, filed on Mar. 14, 2013.

(51) Int. Cl.
  *A61B 17/22*      (2006.01)
  *A61B 17/3207*    (2006.01)
  *A61B 17/32*      (2006.01)

(52) U.S. Cl.
  CPC ......... *A61B 17/320758* (2013.01); *A61B 2017/320004* (2013.01); *A61B 2017/320028* (2013.01);
  (Continued)

(58) Field of Classification Search
  CPC ........ A61B 17/320758; A61B 17/3207; A61B 17/320725; A61B 17/32075; A61B 17/320783; A61B 17/32002; A61B 17/22031; A61B 17/221; A61B 17/34; A61B 17/3403; A61B 17/3405; A61B 17/3409; A61B 17/32; A61B 17/320016; A61B 2017/320766; A61B 2017/320775; A61B 2017/320716; A61B 2017/320733;
  (Continued)

(56) References Cited

U.S. PATENT DOCUMENTS 4,445,509 A    5/1984  Auth
4,850,957 A *  7/1989  Summers ............... A61B 1/12
                                                      418/48

(Continued)

OTHER PUBLICATIONS

International Preliminary Report on Patentability issued in related PCT application No. PCT/US2014/027110, mailed Sep. 24, 2015.

*Primary Examiner* — Darwin Erezo
*Assistant Examiner* — Katherine Schwiker
(74) *Attorney, Agent, or Firm* — Barnes & Thornburg LLP; Jeffrey R. Stone

(57) ABSTRACT

The present invention is directed in various methods, devices and systems relating to rotational atherectomy. More specifically, an oscillating driver is connected to a drive shaft, or torque transfer tube, with abrasive element mounted thereon. The result provides a rotational working diameter for the rotating abrasive element that is larger than its resting diameter. Generally, the preferred abrasive element is concentric in profile and/or with center of mass collinear with the drive shaft's rotational axis. However, eccentric abrasive elements, both in terms of offsetting center of mass and/or geometric eccentricity may also be employed.

10 Claims, 4 Drawing Sheets

(52) U.S. Cl.
CPC ............. *A61B 2017/320733* (2013.01); *A61B 2017/320766* (2013.01)

(58) Field of Classification Search
CPC ....... A61B 2017/320741; A61B 2017/320791; A61B 2017/320004; A61B 2017/320008; A61B 2017/320012; A61B 2017/22039; A61B 2017/22038; A61B 2017/320032; A61B 2017/320024; A61B 2017/320028; A61B 2017/32004; A61B 2017/3405; A61B 2017/3409; A61F 9/00763; A61F 2/01; A61F 2/013; A61F 2002/011
USPC .................. 606/159, 170, 180, 167; 604/22; 15/104.09, 104.13, 104.14, 104.15
See application file for complete search history.

(56) References Cited

U.S. PATENT DOCUMENTS

| | | |
|---|---|---|
| 4,990,134 A | 2/1991 | Auth |
| 5,026,384 A | 6/1991 | Farr et al. |
| 5,030,201 A | 7/1991 | Palestrant |
| 5,041,082 A | 8/1991 | Shiber |
| 5,078,723 A | 1/1992 | Dance et al. |
| 5,087,265 A | 2/1992 | Summers |
| 5,100,425 A | 3/1992 | Fischell et al. |
| 5,116,352 A | 5/1992 | Schnepp-Pesch et al. |
| 5,158,564 A | 10/1992 | Schnepp-Pesch et al. |
| 5,217,474 A | 6/1993 | Zacca et al. |
| 5,242,460 A | 9/1993 | Klein et al. |
| 5,308,354 A | 5/1994 | Zacca et al. |
| 5,312,427 A | 5/1994 | Shturman |
| 5,314,438 A | 5/1994 | Shturman |
| 5,360,432 A | 11/1994 | Shturman |
| 5,370,651 A | 12/1994 | Summers |
| 5,431,673 A | 7/1995 | Summers et al. |
| 5,490,859 A | 2/1996 | Mische et al. |
| 5,501,694 A | 3/1996 | Ressemann et al. |
| 5,540,707 A | 7/1996 | Ressemann et al. |
| 5,554,163 A | 9/1996 | Shturman |
| 5,584,843 A | 12/1996 | Wulfman et al. |
| 5,662,603 A | 9/1997 | Gelbfish |
| 5,792,157 A | 8/1998 | Mische et al. |
| 5,836,868 A | 11/1998 | Ressemann et al. |
| 5,843,103 A | 12/1998 | Wulfman |
| 6,096,054 A * | 8/2000 | Wyzgala ........ A61B 17/320725 606/170 |
| 6,113,615 A * | 9/2000 | Wulfman ....... A61B 17/320758 606/159 |
| 6,146,395 A | 11/2000 | Kanz et al. |
| 6,416,523 B1 | 7/2002 | Lafontaine |
| 6,428,551 B1 | 8/2002 | Hall et al. |
| 6,494,890 B1 | 12/2002 | Shturman et al. |
| 6,497,711 B1 * | 12/2002 | Plaia .............. A61B 17/320725 606/159 |
| 6,554,846 B2 | 4/2003 | Hamilton et al. |
| 6,596,005 B1 | 7/2003 | Kanz et al. |
| 6,758,851 B2 | 7/2004 | Shiber |
| 7,037,316 B2 | 5/2006 | McGuckin, Jr. et al. |
| 7,507,245 B2 | 3/2009 | Shturman et al. |
| 8,137,370 B2 | 3/2012 | Deng |
| 8,177,801 B2 | 5/2012 | Kallok et al. |
| 8,337,516 B2 | 12/2012 | Escudero et al. |
| 8,348,965 B2 | 1/2013 | Prudnikov et al. |
| 8,353,923 B2 | 1/2013 | Shturman |
| 8,551,128 B2 | 10/2013 | Hanson et al. |
| 8,597,313 B2 | 12/2013 | Thatcher et al. |
| 8,628,551 B2 | 1/2014 | Hanson et al. |
| 2001/0004700 A1 | 6/2001 | Honeycutt et al. |
| 2003/0065350 A1 | 4/2003 | Hamilton et al. |
| 2003/0199889 A1 | 10/2003 | Kanz et al. |
| 2004/0147934 A1 | 7/2004 | Kiester |
| 2005/0149084 A1 | 7/2005 | Kanz et al. |
| 2008/0161840 A1 | 7/2008 | Osiroff et al. |
| 2008/0306498 A1 | 12/2008 | Thatcher et al. |
| 2009/0069829 A1 | 3/2009 | Shturman |
| 2009/0105736 A1 | 4/2009 | Prudnikov et al. |
| 2009/0149877 A1 | 6/2009 | Hanson et al. |
| 2009/0299392 A1 | 12/2009 | Rivers |
| 2009/0306689 A1 * | 12/2009 | Welty ............. A61B 17/320725 606/159 |
| 2009/0306691 A1 | 12/2009 | Cambronne et al. |
| 2010/0010492 A1 | 1/2010 | Lockard et al. |
| 2010/0121361 A1 * | 5/2010 | Plowe ............ A61B 17/320758 606/159 |
| 2011/0202079 A1 * | 8/2011 | Schoenle ........ A61B 17/320758 606/159 |
| 2011/0213391 A1 | 9/2011 | Rivers et al. |
| 2012/0191113 A1 | 7/2012 | Shturman |
| 2013/0018398 A1 | 1/2013 | Rivers et al. |
| 2013/0018399 A1 | 1/2013 | Rivers et al. |
| 2013/0023913 A1 | 1/2013 | Rivers et al. |
| 2013/0253552 A1 | 9/2013 | Schoenle et al. |
| 2014/0005699 A1 | 1/2014 | Bonnette et al. |

\* cited by examiner

DEVICES, SYSTEMS AND METHODS FOR AN OSCILLATING CROWN DRIVE FOR ROTATIONAL ATHERECTOMY

CROSS-REFERENCE TO RELATED APPLICATIONS

This application claims priority to App. Ser. No. 61/782,184, entitled "Devices, Systems and Methods for an Oscillating Crown Drive for Rotational Atherectomy," filed Mar. 14, 2013, the entire contents of which are hereby incorporated by reference.

FIELD OF THE INVENTION

The present disclosure generally relates to devices and systems relating to rotational atherectomy. More specifically, an oscillating driver is connected to a drive shaft with an abrading head mounted thereon. The result provides a rotational working diameter for the rotating abrasive element that is larger than its resting diameter.

DESCRIPTION OF THE RELATED ART

A variety of techniques and instruments have been developed for use in the removal or repair of tissue in arteries and similar body passageways. A frequent objective of such techniques and instruments is the removal of atherosclerotic plaques in a patient's arteries. Atherosclerosis is characterized by the buildup of fatty deposits (atheromas) in the intimal layer (under the endothelium) of a patient's blood vessels. Very often over time, what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

Rotational atherectomy procedures have become a common technique for removing such stenotic material. Such procedures are used most frequently to initiate the opening of calcified lesions in coronary arteries. Most often the rotational atherectomy procedure is not used alone, but is followed by a balloon angioplasty procedure, which, in turn, is very frequently followed by placement of a stent to assist in maintaining patentcy of the opened artery. For non-calcified lesions, balloon angioplasty most often is used alone to open the artery, and stents often are placed to maintain patentcy of the opened artery. Studies have shown, however, that a significant percentage of patients who have undergone balloon angioplasty and had a stent placed in an artery experience stent restenosis—i.e., blockage of the stent which most frequently develops over a period of time as a result of excessive growth of scar tissue within the stent. In such situations an atherectomy procedure is the preferred procedure to remove the excessive scar tissue from the stent (balloon angioplasty being not very effective within the stent), thereby restoring the patentcy of the artery.

Several kinds of rotational atherectomy devices have been developed for attempting to remove stenotic material. In one type of device, such as that shown in U.S. Pat. No. 4,990,134 (Auth), a burr covered with an abrasive abrading material such as diamond particles is carried at the distal end of a flexible drive shaft. The burr is rotated at high speeds (typically, e.g., in the range of about 150,000-190,000 rpm) while it is advanced across the stenosis. As the burr is removing stenotic tissue, however, it blocks blood flow. Once the burr has been advanced across the stenosis, the artery will have been opened to a diameter equal to or only slightly larger than the maximum outer diameter of the burr. Frequently more than one size burr must be utilized to open an artery to the desired diameter.

U.S. Pat. No. 5,314,438 (Shturman) discloses another atherectomy device having a drive shaft with a section of the drive shaft having an enlarged diameter, at least a segment of this enlarged surface being covered with an abrasive material to define an abrasive segment of the drive shaft. When rotated at high speeds, the abrasive segment is capable of removing stenotic tissue from an artery. Though this atherectomy device possesses certain advantages over the Auth device due to its flexibility, it also is capable only of opening an artery to a diameter about equal to the diameter of the enlarged abrading surface of the drive shaft since the device is not eccentric in nature.

U.S. Pat. No. 6,494,890 (Shturman) discloses a known atherectomy device having a drive shaft with an enlarged eccentric section, wherein at least a segment of this enlarged section is covered with an abrasive material. When rotated at high speeds, the abrasive segment is capable of removing stenotic tissue from an artery. The device is capable of opening an artery to a diameter that is larger than the resting diameter of the enlarged eccentric section due, in part, to the orbital rotational motion during high speed operation. Since the enlarged eccentric section comprises drive shaft wires that are not bound together, the enlarged eccentric section of the drive shaft may flex during placement within the stenosis or during high speed operation. This flexion allows for a larger diameter opening during high speed operation, but may also provide less control than desired over the diameter of the artery actually abraded. In addition, some stenotic tissue may block the passageway so completely that the Shturman device cannot be placed therethrough. Since Shturman requires that the enlarged eccentric section of the drive shaft be placed within the stenotic tissue to achieve abrasion, it will be less effective in cases where the enlarged eccentric section is prevented from moving into the stenosis. The disclosure of U.S. Pat. No. 6,494,890 is hereby incorporated by reference in its entirety.

U.S. Pat No. 5,681,336 (Clement) provides a known eccentric tissue removing burr with a coating of abrasive particles secured to a portion of its outer surface by a suitable binding material. This construction is limited, however because, as Clement explains at Col. 3, lines 53-55, that the asymmetrical burr is rotated at "lower speeds than are used with high speed ablation devices, to compensate for heat or imbalance." That is, given both the size and mass of the solid burr, it is infeasible to rotate the burr at the high speeds used during atherectomy procedures, i.e., 20,000-200,000 rpm. Essentially, the center of mass offset from the rotational axis of the drive shaft would result in development of significant centrifugal force, exerting too much pressure on the wall of the artery and creating too much heat and excessively large particles.

Thus, a need exists in the art generally for a rotational atherectomy device, system and method that allows for increasing the working diameter of an abrading head.

BRIEF SUMMARY OF THE INVENTION

The present invention is directed in various methods, devices and systems relating to rotational atherectomy. More specifically, an oscillating driver is connected to a drive shaft, or torque transfer tube, with abrasive element mounted thereon. The result provides a rotational working diameter for the rotating abrasive element that is larger than its resting diameter. Generally, the preferred abrasive element is concentric in profile and/or with center of mass collinear with the drive shaft's rotational axis. However, eccentric abrasive elements, both in terms of offsetting center of mass and/or geometric eccentricity may also be employed.

DETAILED DESCRIPTION

Figure 1:
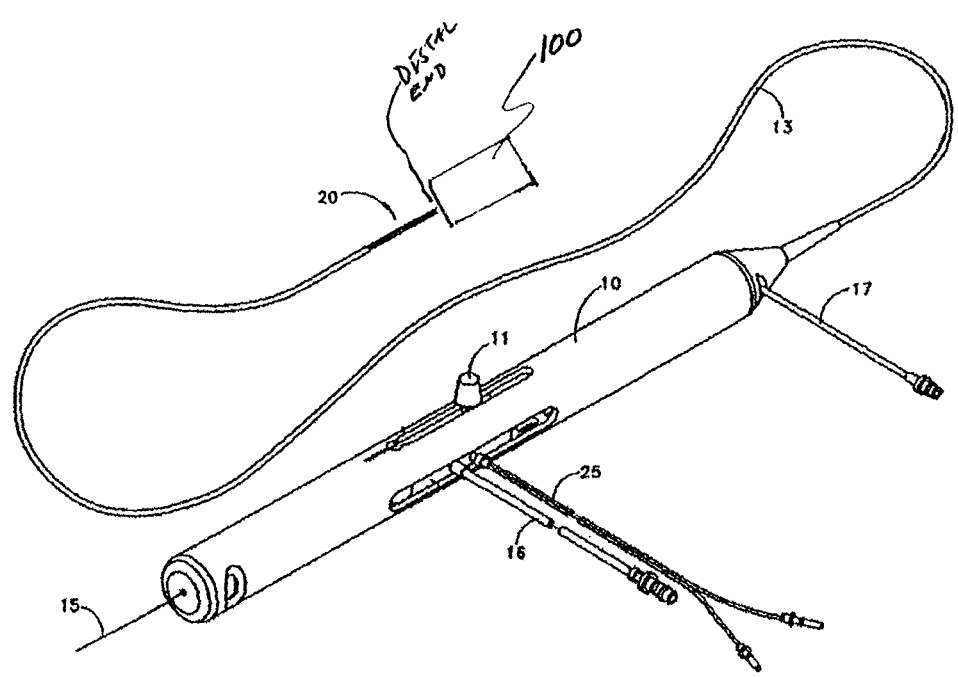
FIG. 1 illustrates a perspective view of one embodiment of the present invention.

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

The present invention provides a

Various embodiments of the present invention may be incorporated into a rotational atherectomy system as described generally in U.S. Pat. No. 6,494,890, entitled "ECCENTRIC ROTATIONAL ATHERECTOMY DEVICE," which is incorporated herein by reference. Additionally, the disclosure of the following co-owned patents or patent applications are herein incorporated by reference in their entireties: U.S. Pat. No. 6,295,712, entitled "ROTATIONAL ATHERECTOMY DEVICE"; U.S. Pat. No. 6,132,444, entitled "ECCENTRIC DRIVE SHAFT FOR ATHERECTOMY DEVICE AND METHOD FOR MANUFACTURE"; U.S. Pat. No. 6,638,288, entitled "ECCENTRIC DRIVE SHAFT FOR ATHERECTOMY DEVICE AND METHOD FOR MANUFACTURE"; U.S. Pat. No. 5,314,438, entitled "ABRASIVE DRIVE SHAFT DEVICE FOR ROTATIONAL ATHERECTOMY"; U.S. Pat. No. 6,217,595, entitled "ROTATIONAL ATHERECTOMY DEVICE"; U.S. Pat. No. 5,554,163, entitled "ATHERECTOMY DEVICE"; U.S. Pat. No. 7,507,245, entitled "ROTATIONAL ANGIOPLASTY DEVICE WITH ABRASIVE CROWN"; U.S. Pat. No. 6,129,734, entitled "ROTATIONAL ATHERECTOMY DEVICE WITH RADIALLY EXPANDABLE PRIME MOVER COUPLING"; U.S. Pat. No. 8,597,313, entitled "ECCENTRIC ABRADING HEAD FOR HIGH-SPEED ROTATIONAL ATHERECTOMY DEVICES"; U.S. Pat. No. 8,439,937, entitled "SYSTEM, APPARATUS AND METHOD FOR OPENING AN OCCLUDED LESION"; U.S. Pat. Pub. No. 2009/0299392, entitled "ECCENTRIC ABRADING ELEMENT FOR HIGH-SPEED ROTATIONAL ATHERECTOMY DEVICES"; U.S. Pat. Pub. No. 2010/0198239, entitled "MULTI-MATERIAL ABRADING HEAD FOR ATHERECTOMY DEVICES HAVING LATERALLY DISPLACED CENTER OF MASS"; U.S. Pat. Pub. No. 2010/0036402, entitled "ROTATIONAL ATHERECTOMY DEVICE WITH PRE-CURVED DRIVE SHAFT"; U.S. Pat. Pub. No. 2009/0299391, entitled "ECCENTRIC ABRADING AND CUTTING HEAD FOR HIGH-SPEED ROTATIONAL ATHERECTOMY DEVICES"; U.S. Pat. Pub. No. 2010/0100110, entitled "ECCENTRIC ABRADING AND CUTTING HEAD FOR HIGH-SPEED ROTATIONAL ATHERECTOMY DEVICES"; U.S. Design Pat. No. D610258, entitled "ROTATIONAL ATHERECTOMY ABRASIVE CROWN"; U.S. Design Pat. No. D6107102, entitled "ROTATIONAL ATHERECTOMY ABRASIVE CROWN"; U.S. Pat. Pub. No. 2009/0306689, entitled "BIDIRECTIONAL EXPANDABLE HEAD FOR ROTATIONAL ATHERECTOMY DEVICE"; U.S. Pat. Pub. No. 2010/0211088, entitled "ROTATIONAL ATHERECTOMY SEGMENTED ABRADING HEAD AND METHOD TO IMPROVE ABRADING EFFICIENCY"; U.S. Pat. Pub. No. 2013/0018398, entitled "ROTATIONAL ATHERECTOMY DEVICE WITH ELECTRIC MOTOR"; and U.S. Pat. No. 7,666,202, entitled "ORBITAL ATHERECTOMY DEVICE GUIDE WIRE DESIGN." It is contemplated by this invention that the features of one or more of the embodiments of the present invention may be combined with one or more features of the embodiments of atherectomy devices described therein.

FIG. 1 illustrates one embodiment of a rotational atherectomy device according to the present invention. The device includes a handle portion 10; an elongated, flexible non-oscillating and therefore fixed axis drive shaft 20 with a lumen therethrough for passage of a guidewire and further having an oscillating section 100 attached thereto proximate to the distal end of the drive shaft 20 and comprising a radially offsetting driveshaft attachment 102 and abrading head 106 mounted or otherwise disposed on a flexible oscillating drive shaft 110. Oscillating section 100 and its components and functionality will be discussed in further detail below. Elongated catheter 13 is also illustrated as extending distally from the handle portion 10. The non-oscillating fixed axis drive shaft 20 is constructed from helically coiled wire as is known in the art and has an outer surface 24 and an inner surface 22 defining an inner lumen, permitting the non-oscillating drive shaft 20 to be advanced and rotated over a guide wire. The catheter 13 has a lumen in which most of the length of the drive shaft 20 is disposed, except for the oscillating section 100. A fluid supply line 17 may be provided for introducing a cooling and lubricating solution (typically saline or another biocompatible fluid) into the catheter 13.

The handle 10 desirably contains a turbine (or similar rotational drive mechanism) for rotating the drive shaft 20 at high speeds. The handle 10 typically may be connected to a power source, such as compressed air delivered through a tube 16. A pair of fiber optic cables 25, alternatively a single fiber optic cable may be used, may also be provided for monitoring the speed of rotation of the turbine and drive shaft 20 (details regarding such handles and associated instrumentation are well known in the industry. The handle 10 also desirably includes a control knob 11 for advancing and retracting the turbine and drive shaft 20 and attached oscillating section 100 with respect to the catheter 13 and the body of the handle.

Figure 2:
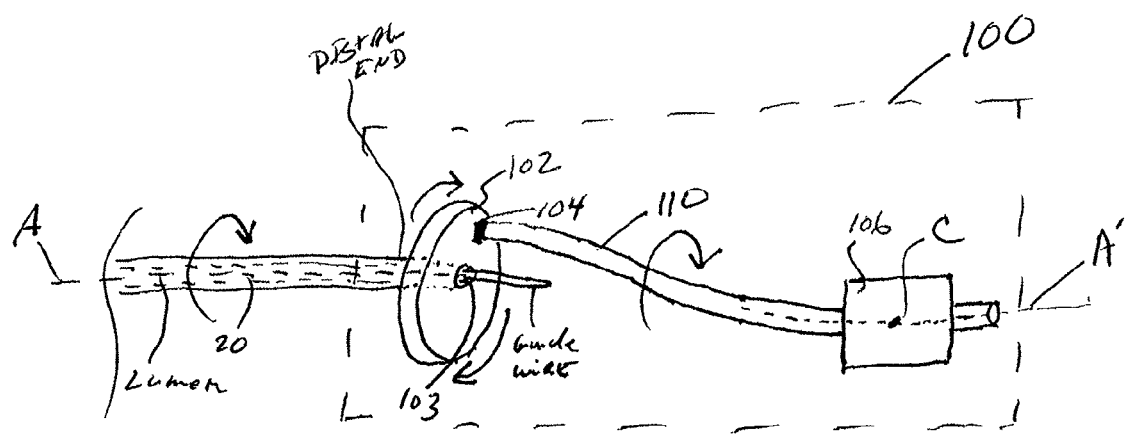
FIG. 2 illustrates a partial cutaway and side view of one embodiment of the present invention.

Turning now to FIG. 2, the oscillating section 100 is attached proximate to the distal end of the non-oscillating drive shaft 20 and comprises the radially offsetting driveshaft attachment 102 and abrading head 106 mounted or otherwise disposed on a flexible oscillating drive shaft 110, the flexible oscillating drive shaft 110 is attached to the radially offsetting drive shaft attachment 102 at attachment point 104 in a fixed and non-sliding attachment as illustrated. The flexible oscillating drive shaft 110 is shown as extending longitudinally and distally away from attachment point 104 when the rotational atherectomy system is not rotating as well as during high-speed rotation as shown in FIG. 2. Abrading head 106 is, as illustrated, spaced longitudinally distally away from the attachment point 104 and from the radially offsetting drive shaft attachment 102 as well as the distal end of the non-oscillating drive shaft 102 when the rotational atherectomy system is not rotating as well as during high-speed rotation as shown in FIG. 2.

The radially offsetting drive shaft attachment 102 comprises, as illustrated, a circular structure with a centered lumen 103 therethrough which is coincident and in fluid communication with the non-oscillating drive shaft 20 lumen. In this configuration, as the non-oscillating drive shaft 20 rotates, the radially offsetting drive shaft attachment 102 will spin concentrically with the drive shaft 20 because the center of mass of the circular drive shaft attachment 102 is also coincident with the rotational axis A of the non-oscillating drive shaft 20. FIG. 2 illustrates that the guidewire may pass through non-oscillating drive shaft 20 lumen as well as through centered lumen 103. The skilled artisan will recognize that the circular form of the illustrated embodiment of drive shaft attachment 102 is but one of several forms that are functionally possible. What is required is that the center of mass of the drive shaft attachment 102 is located in the center of the centered lumen 103.

The flexible oscillating drive shaft 110 is attached to the radially offsetting drive shaft attachment 102 at an attachment point 104 radially offset from the centered lumen 103. The distance of this radial offset, together with the rotational speed of the drive shaft 20, and therefore oscillating section 100, and the mass, and location thereof, of the abrading head 106 determine the working diameter of the abrading head 106 during operation. An increase in working diameter of the abrading head 106 is directly related to greater distance between attachment point 104 and centered lumen 103, increasing rotational speed of drive shaft 20 and oscillating section 100, and increased mass and radially offsetting of the increased mass of abrading head 106. Further, as discussed below, the location of the radially offset center of mass C and the attachment point 104 relative to each other in a longitudinal plane also has a direct effect on the flexing of oscillating drive shaft 110 and, therefore, the magnitude of the working diameter achieved by the abrading head 106 during rotational operation.

Figure 3:
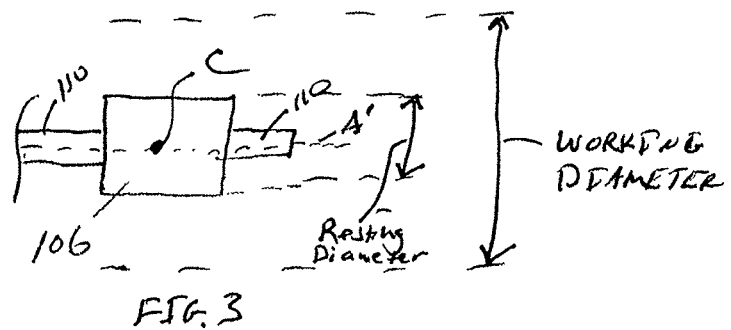
FIG. 3 illustrates a partial cutaway and side view of one embodiment of the present invention.

The abrading head 106 is illustrated in FIGS. 2 and 3 as a concentric, i.e., longitudinally and laterally or radially symmetrical construction about the oscillating drive shaft 110 to which it is attached by means well understood in the art. As a result, the center of mass C of abrading head 106 is, in FIGS. 2 and 3, coincident with the rotational axis A' of oscillating drive shaft 110.

Figure 4:
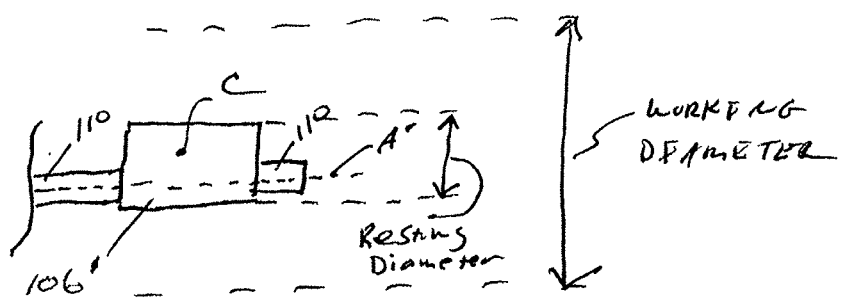
FIG. 4 illustrates a partial cutaway and side view of one embodiment of the present invention.

Alternatively, as shown in FIG. 4, abrading head 106 may comprise a center of mass C that is radially offset from the rotational axis A' of oscillating drive shaft 110. The skilled artisan will recognize that the center of mass C may be moved radially away with respect to the rotational axis A' of oscillating drive shaft 110 by creating a purely geometric eccentricity as illustrated in FIG. 4 having at least a radial or lateral geometric asymmetry or by using materials of differing density in either a geometrically concentric or eccentric abrading head 106.

Figure 5:
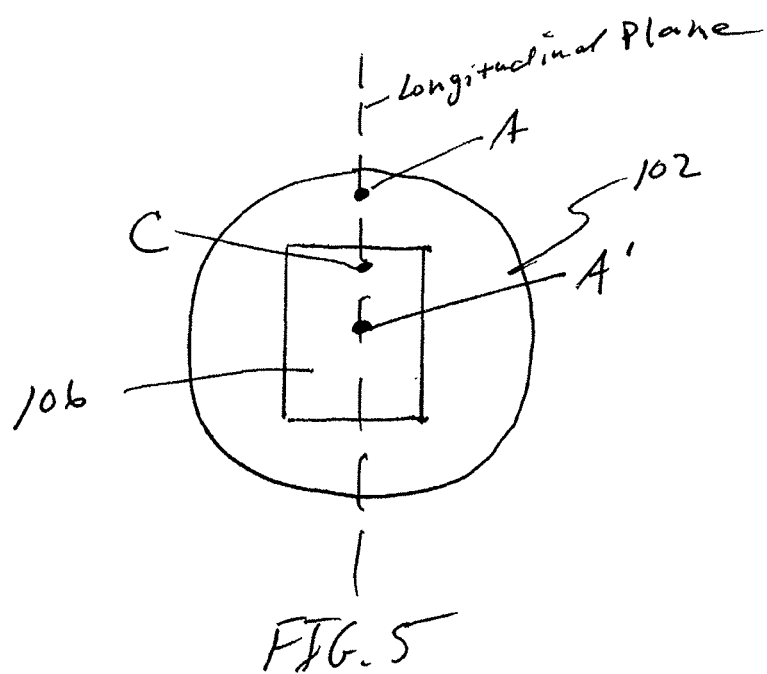
FIG. 5 illustrates an end view of one embodiment of the present invention.

In both cases, as shown, the working diameter achieved by abrading head 106 is greater than its resting diameter. A damping effect may be added to the oscillating section 100 using the technique illustrated in FIG. 4 by aligning the radially offset center of mass C of abrading head 106 with the attachment point 104 of radially offsetting drive shaft attachment 102 so that there is a 0-degree offset between attachment point 104 and radially offset center of mass C in the longitudinal plane as in FIG. 5.

Figure 6:
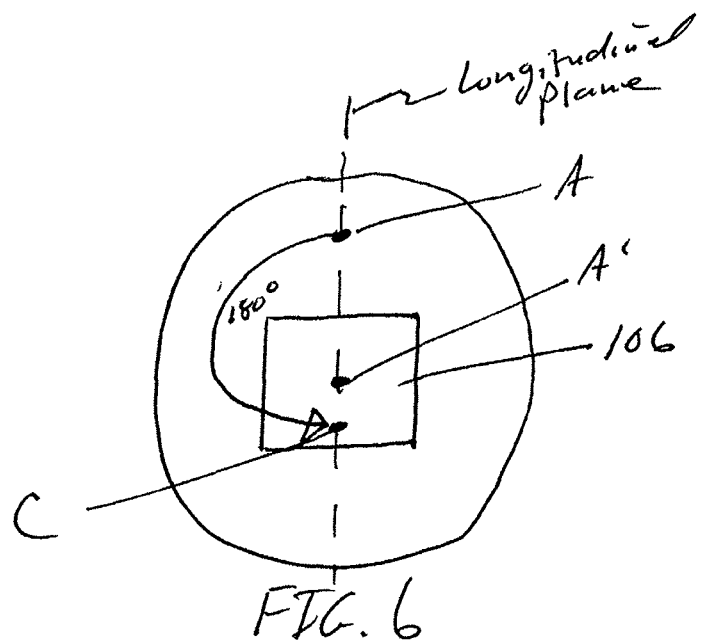
FIG. 6 illustrates an end view of one embodiment of the present invention.

Alternatively, as in FIG. 6 the flexing of oscillating drive shaft 110 may be enhanced by shifting the radially offset center of mass C of abrading head 106 180-degrees so that the radially offset center of mass is located on the opposite side of oscillating drive shaft's axis of rotation A' as compared with attachment point 104.

In all cases, whether abrading head 106 is concentric or eccentric, the working diameter achieved during high speed rotation is greater than the working diameter of abrading head 106.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. A rotational atherectomy system adapted for high-speed rotation and having an abrasive head adapted to move from a resting diameter when there is no system rotation to a working diameter greater than the resting diameter during high-speed rotation of the system, comprising:
    an elongated flexible non-oscillating drive shaft having a lumen therethrough, a rotational axis and a distal end; and
    an oscillating section attached proximate the distal end of the elongated non-oscillating drive shaft and comprising:
        a radially offsetting drive shaft attachment attached to the non-oscillating drive shaft and having a centered lumen therethrough, the centered lumen in fluid communication with the lumen of the non-oscillating drive shaft and further being coincident with the rotational axis of the non-oscillating drive shaft, and an attachment point radially offset from the centered lumen, and
        a flexible oscillating drive shaft directly attached to the attachment point of the radially offsetting drive shaft attachment and extending distally and longitudinally therefrom; and
        the abrading head attached to the flexible oscillating drive shaft and spaced distally from the attachment point.

2. The rotational atherectomy system of claim 1, wherein the radially offsetting drive shaft attachment is circular.

3. The rotational atherectomy system of claim 1, further comprising the oscillating drive shaft having a rotational axis.

4. The rotational atherectomy system of claim 3, further comprising the abrading head being concentric and comprising a center of mass that is coincident with the rotational axis of the oscillating drive shaft.

5. The rotational atherectomy system of claim 3, further comprising the abrading head being concentric and having a center of mass that is radially offset from the rotational axis of the oscillating drive shaft.

6. The rotational atherectomy system of claim 3, further comprising the abrading head being eccentric and comprising a center of mass that is radially offset from the rotational axis of the oscillating drive shaft.

7. The rotational atherectomy system of claim 6, wherein the abrading head is geometrically eccentric.

8. The rotational atherectomy system of claim 6, further comprising the radially offset attachment point and the eccentric abrading head's center of mass that is radially offset from the rotational axis of the oscillating drive shaft aligned longitudinally within a longitudinal plane through the radially offsetting drive shaft attachment.

9. The rotational atherectomy system of claim 8, further comprising a zero degree radial offset between the longitudinally aligned radially offset attachment point and the radially offset center of mass.

10. The rotational atherectomy system of claim 8, further comprising a 180-degree radial offset between the longitudinally aligned radially offset attachment point and the radially offset center of mass.

\* \* \* \* \*